United States Patent [19]

Gustafson et al.

[11] Patent Number: 5,319,129

[45] Date of Patent: Jun. 7, 1994

[54] PREPARATION OF DIMETHYL CYCLOHEXANEDICARBOXYLATES

[75] Inventors: Bruce L. Gustafson; Yeong-Jen Kuo; Brent A. Tennant, all of Kingsport, Tenn.

[73] Assignee: Eastman Kodak Company, Rochester, N.Y.

[21] Appl. No.: 76,674

[22] Filed: Jun. 15, 1993

[51] Int. Cl.⁵ .............................. C07C 69/74
[52] U.S. Cl. ................................. 560/127
[58] Field of Search ......................... 560/127

[56] References Cited

U.S. PATENT DOCUMENTS

| | | | |
|---|---|---|---|
| 2,675,390 | 4/1954 | Rosenblatt | 560/127 |
| 2,794,030 | 5/1957 | Phillips et al. | 560/127 |
| 3,027,398 | 3/1962 | Foohey | 260/468 |
| 3,334,149 | 8/1967 | Akin et al. | 260/617 |
| 3,428,668 | 2/1969 | Huelsmann et al. | 260/468 |
| 3,444,232 | 5/1969 | Jaffe | 560/127 |
| 4,024,173 | 5/1977 | Lenz et al. | 260/468 |

FOREIGN PATENT DOCUMENTS

| | | |
|---|---|---|
| 1306408 | 11/1989 | Japan . |
| 0817736 | 8/1959 | United Kingdom . |
| 1026635 | 4/1966 | United Kingdom . |

*Primary Examiner*—Paul J. Killos
*Attorney, Agent, or Firm*—J. Frederick Thomsen; William P. Heath, Jr.

[57] ABSTRACT

Disclosed is a process for the preparation of a dimethyl cyclohexanedicarboxylate by the hydrogenation of the analogous dimethyl benzenedicarboxylate ester in the presence of a class of palladium on alumina catalysts which have a unique combination of characteristics. The use of the catalysts permits the process to be carried out at significantly lower process pressures.

8 Claims, No Drawings

PREPARATION OF DIMETHYL CYCLOHEXANEDICARBOXYLATES

This invention pertains to an improved process for the preparation of dimethyl cyclohexanedicarboxylates by the hydrogenation of the analogous dimethyl benzenedicarboxylate ester. More specifically, the present invention pertains to an improved process for the hydrogenation of a dimethyl benzenedicarboxylate ester in the presence of certain, supported palladium catalysts which permit the use of significantly lower process pressures.

Dimethyl 1,4-cyclohexanedicarboxylate has been manufactured for over 30 years as an intermediate in the production of cyclohexanedimethanol which is used extensively as a monomer in the preparation of condensation polymers, particularly polyesters. Dimethyl cyclohexanedicarboxylates are valuable chemical intermediates useful, for example, in the manufacture of polyester resins used in the formulation of coating compositions.

The manufacture of dimethyl 1,4-cyclohexanedicarboxylate and 1,4-cyclohexanedimethanol using dimethyl terephthalate as the feedstock and a heterogenous mode of operation is described in U.S. Pat. No. 3,334,149. This process requires the use of high pressures, e.g., greater than 346 bars absolute, and utilizes a palladium on alumina catalyst in the hydrogenation of dimethyl terephthalate to dimethyl 1,4-cyclohexanedicarboxylate. The specific palladium on alumina employed contains 0.5 weight percent palladium deposited on alumina, the crystalline phase of which is a mixture of bayerite and boehmite. The catalyst is used in the form of 3 mm chips and exhibits poor physical strength.

It is apparent that chemical processes which require the use of high pressures such as pressures in excess of 340 bars are inherently expensive due to the increased operating costs and the cost of the apparatus required including the high pressure rated reactor and the compressors. It has been found, however, that when the hydrogenation of dimethyl terephthalate to dimethyl 1,4-cyclohexanedicarboxylate is carried out at pressures less than 135 bars absolute using the above described palladium on alumina catalyst, commercially acceptable hydrogenation rates cannot achieved over an extended period of time. For example, when operating continuously at 125 bars absolute using the above-described catalyst, the process is unstable and the hydrogenation rate typically is not more than approximately 55% of the rates achieved at approximately 410 bars absolute pressure. The reduced hydrogenation rate is due to decreased activity of the palladium catalyst which, we believe, is related to the generation of carbon monoxide during the hydrogenation at lower pressures. It is known that the presence of carbon monoxide in hydrogen gas used in hydrogenation processes is detrimental to such processes. However, the extreme sensitivity of the above described palladium on alumina catalyst to parts per million (ppm) amounts of carbon monoxide is surprising.

The present invention is concerned with a process whereby dimethyl benzenedicarboxylates may be catalytically hydrogenated to the corresponding dimethyl cyclohexanedicarboxylate using moderate pressures and readily available catalysts. We have discovered that acceptable rates at moderate pressures may be achieved by the use of palladium on alumina catalysts wherein (1) the dispersion and depth of deposition of the palladium metal are within certain ranges, (2) the alumina is of a particular crystalline phase, and (3) the surface area of the catalyst is within a particular range. The process provided by our invention therefore provides a means for the preparation of a dimethyl cyclohexanedicarboxylate which comprises contacting a dimethyl benzenedicarboxylate with hydrogen at a temperature of about 140° to 400° C. and a pressure of about 10 to 200 bars absolute in the presence of a palladium on alumina catalyst; wherein (1) palladium comprises about 0.1 to 5.0 weight percent of the catalyst;
(2) the palladium dispersion is at least 20 percent;
(3) at least 90 weight percent of the palladium is located on the alumina at a depth less than 200 microns from the surface of the alumina; and
(4) the crystalline phase of the alumina is alpha, theta, delta, gamma, eta or a mixture thereof.

The minimum temperature at which the process may be carried out is limited by the melting point of the dimethyl benzenedicarboxylate reactant, e.g., 140° C. for dimethyl 1,4-benzenedicarboxylate (dimethyl terephthalate). The maximum operating temperature can be as high as 400° C. The process preferably is carried out at a temperature in the range of about 140° to 250° C. Although the process may be carried out at pressures in the range of about 8 to 690 bars absolute, the present invention permits the achievement of good hydrogenation rates without the use of the high pressures described in the literature. Thus, the preferred pressures are within the range of about 50 to 170 bars absolute. Although the 1,2- , 1,3- and 1,4-isomers of dimethyl cyclohexanedicarboxylate may be prepared by the process of this invention by the hydrogenation of the analogous dimethyl benzenedicarboxylate, the primary usefulness of the process is in the manufacture of the 1,3- and, especially, the 1,4-isomers.

The catalyst used in the present invention is palladium deposited on an alumina support wherein the palladium comprises about 0.1 to 5.0, preferably 0.5 to 2.0, weight percent based on the total weight of the catalyst. The dispersion of the palladium on and in the alumina support typically is measured by titration of the surface of the support with carbon monoxide gas and measuring the amount of carbon monoxide adsorbed on the palladium surface. Normally, it is assumed that each surface metal atom will adsorb one molecule of carbon monoxide and thus, the percent of metal exposed may be determined. This percentage is known as the dispersion. See Myasaki, J. Catal., 65, 84 (1980) and "Structure of Metallic Catalysts" by J. R. Anderson, Academic Press, 1975, page 360. The catalysts which are advantageously used in accordance with the present invention have a dispersion percentage of at least 20 percent, preferably at least 30 percent (as determined by carbon monoxide adsorption as described herein).

Another characteristic of the palladium catalyst used in the present invention is that most of the palladium is located on or near the surface of the alumina support. Accordingly, at least 90 weight percent of the palladium is located no deeper than 200 microns, preferably less than 100 microns, from the external surface of the alumina support. As is well-known in the art, depth of impregnation can be determined either visually using optical microscopy or by a line scan technique in a SEM with a palladium sensitive detector. See, for example, the above cited "Structure of Metallic Catalysts".

Yet another important characteristic of the catalysts is the crystalline phase of the alumina support which is selected from the alpha, theta, delta, gamma, eta phases or a mixture of such crystalline phases. Alumina of theta, delta or alpha crystalline phases or mixture of such alumina is preferred with theta alumina being especially preferred.

The nitrogen BET surface area of the palladium on alumina catalysts used in the process of our invention is in the range of about 20 to 300 square meters per gram ($m^2/g$) with the range of about 30 to 150 $m^2/g$ being preferred. It is well known in the art that BET surface area is a function of crystalline phases and calcination history and should be as high as possible while maintaining the appropriate oxide phase. Catalysts having the characteristics described hereinabove may be prepared according to conventional impregnation or deposition techniques using procedures well known to those skilled in the art. The catalyst may be used in the hydrogenation process in the form of pellets, spheres, extrudates and the like. The particular form is not critical so long as the catalyst form does not lead to excessive channeling of the liquid feed through the reactor, e.g., in continuous operation using a fixed bed of catalyst through which the reactant is passed. Preferably, the surface area:volume ratio of the catalyst is at least 500 and preferably greater than 1500.

The process of the invention may be carried out in a batch, semi continuous or continuous mode using conventional chemical processing techniques. The preferred mode of operation is a continuous process wherein a melt of a dimethyl benzenedicarboxylate is passed over and through one or more fixed beds of catalyst in a "trickle bed" manner. Typically, some of the dimethyl cyclohexanedicarboxylate product is recycled to the feed port of the reactor and serves as a solvent for the reactant. Other inert, non aromatic compounds which are liquid under the operating conditions employed may be used as a solvent. The process may be operated in either an adiabatic or isothermal fashion. In trickle bed operation, the liquid hourly space velocity (LHSV; unit volume reactant fed per hour per unit volume catalyst) of the reactant feed may be in the range of about 0.1 to 10 with a preferred range of 0.5 to 5. The LHSV for the total liquid flow (reactant plus solvent) may be in the range of 1 to 30. Hydrogen is fed to the reactor in excess of the stoichiometric quantity and normally is purged from the system. The rate of hydrogen purge is dependent on the temperature and pressure at which the process is operated.

Our novel process is further illustrated by the following examples. All experiments were performed in a trickle bed reactor system comprising a 1.83 meter (6 feet) section of 316 stainless steel pipe having an interior diameter of 2.5 cm (1 inch) and equipped with means for liquid recycle. The catalyst (800 cc) was held in place within the reactor by 100 cc of 1.6 mm (0.0625 inch) 316 stainless steel Penn State packing located above and below the catalyst bed. The temperatures at various points within the catalyst bed were measured by 10 thermocouples which extended through the reactor wall and approximately 3.2 mm into the catalyst. The temperature reported in each example is the average of these 10 readings. Typical temperature gradients through the bed were less than 10° C.

The procedure generally used in each experiment comprised purging the system with nitrogen and pumping dimethyl 1,4-cyclohexanedicarboxylate (DMCD) through the reactor system at a rate of 5 Kg/hour at 150° C. and 70 bars absolute with a 6 L/hour liquid recycle. The feed gas then was switched from nitrogen to hydrogen, the pressure slowly Was increased to 125.1 bars absolute and, finally, the temperature was increased to the desired reaction temperature. The reaction was commenced by switching the reactor feed from DMCD to 30:70 parts by weight mixture of dimethyl terephthalate and DMCD. Hydrogen was purged from the reactor system at a rate of 8 to 10 L/minute. Carbon monoxide concentrations in the hydrogen purge gas were monitored using a Beckman IR carbon monoxide analyzer. Operating data were recorded when a steady state of operation was achieved, typically 1 to 2 hours from the commencement of the reaction.

The palladium on alumina catalysts employed in the examples are described in Table I wherein % Pd is the weight percent palladium present on the catalyst, BET SA is the BET surface area of the catalyst in $m^2/g$, Pd Disp. is the percent of the palladium which is exposed, Impreg. Depth is the depth in microns of the impregnation of the palladium on and in the support, and Phase is the crystalline phase of the alumina support.

TABLE I

| Catalyst | % Pd | BET SA | Pd Disp. | Impreg. Depth | Phase |
|---|---|---|---|---|---|
| A | 0.75 | 42 | 29 | 40 | Alpha, Theta |
| B | 0.50 | 34 | 27 | 62 | Alpha, Theta |
| C | 1.00 | 107 | 30 | 50–100 | Alpha, Theta |
| D | 0.50 | 270 | 32 | 62 | Boehmite |
| E | 0.75 | 93 | 28 | 400 | Theta |
| F | 0.75 | 203 | — | 150 | Gamma |
| G | 0.75 | 198 | 11 | <100 | Theta |

EXAMPLES 1–3 AND COMPARATIVE EXAMPLE 1–4

Dimethyl terephthalate was hydrogenated to DMCD using the catalysts and the procedure described hereinabove. The catalyst and temperature (°C., Temp.) used in each example are set forth in Table II wherein C-1 through C-4 designate the comparative examples, DMT in Product is the weight percent of the product which consists of unconverted dimethyl terephthalate, STY is the space time yield of DMCD in g DMCD per cc catalyst-hour, and CO is the concentration in ppm of carbon monoxide in the hydrogen purge gas.

TABLE II

| Example | Catalyst | Temp. | DMT in Product | STY | CO |
|---|---|---|---|---|---|
| 1 | A | 177 | 0.0 | 1.87 | 15 |
| 2 | B | 170 | 2.2 | 1.73 | 16 |
| 3 | C | 175 | 0.7 | 1.82 | 7 |
| C-1 | D | 173 | 7.4 | 1.41 | 40 |
| C-2 | E | 172 | 6.1 | 1.49 | 26 |
| C-3 | F | 170 | 10.0 | 1.25 | 28 |
| C-4 | G | 170 | >10 | <1.25 | 15 |

The space time yields reported in Table II demonstrate the advantages provided by the present invention utilizing Catalyst A, B or C. The relatively poor performance of Catalysts D, E and F is not completely illustrated by Comparative Examples 1-3 since the gaseous effluent from the reactor was not recycled in the examples reported herein. We have found that in similar experiments in which the gaseous reactor effluent is recycled in a manner analogous to commercial operation, the presence of 37 ppm carbon monoxide in the recycled gas can decrease production rates as much as 15%.

The invention has been described in detail with particular reference to preferred embodiments thereof, but it will be understood that variations and modifications can be effected within the spirit and scope of the invention.

We claim:

1. Process for the preparation of a dimethyl cyclohexanedicarboxylate which comprises contacting a dimethyl benzenedicarboxylate with hydrogen at a temperature of about 140° to 400° C. and a pressure of about 10 to 200 bars absolute in the presence of a palladium on alumina catalyst; wherein
   (1) palladium comprises about 0.1 to 5.0 weight percent of the catalyst;
   (2) the palladium dispersion is at least 20 percent;
   (3) at least 90 weight percent of the palladium is located on the alumina at a depth less than 200 microns from the surface of the alumina; and
   (4) the crystalline phase of the alumina is alpha, theta, delta, gamma, eta or a mixture thereof.

2. Process according to claim 1 which comprises contacting a dimethyl benzenedicarboxylate with hydrogen at a temperature of about 140° to 400° C. and a pressure of about 10 to 200 bars absolute in the presence of a palladium on alumina catalyst; wherein
   (1) palladium comprises about 0.5 to 2.0 weight percent of the catalyst;
   (2) the palladium dispersion is at least 30 percent;
   (3) at least 90 weight percent of the palladium is located on the alumina at a depth less than 100 microns from the surface of the alumina; and
   (4) the crystalline phase of the alumina is alpha, theta, delta or a mixture thereof.

3. Process according to claim 2 wherein a solution of the dimethyl benzenedicarboxylate in dimethyl cyclohexanedicarboxylate is contacted with hydrogen.

4. Process for the preparation of a dimethyl cyclohexanedicarboxylate which comprises contacting a dimethyl benzenedicarboxylate with hydrogen at a temperature of about 140 to 400° C. and a pressure of about 50 to 170 bars absolute in the presence of a palladium on alumina catalyst; wherein
   (1) palladium comprises about 0.1 to 5.0 weight percent of the catalyst;
   (2) the palladium dispersion is at least 20 percent;
   (3) at least 90 weight percent of the palladium is located on the alumina at a depth less than 200 microns from the surface of the alumina; and
   (4) the crystalline phase of the alumina is alpha, theta, delta, gamma, eta or a mixture thereof.

5. Process according to claim 4 which comprises contacting a dimethyl benzenedicarboxylate with hydrogen at a temperature of about 140° to 250° C. and a pressure of about 50 to 170 bars absolute in the presence of a palladium on alumina catalyst; wherein
   (1) palladium comprises about 0.5 to 2.0 weight percent of the catalyst;
   (2) the palladium dispersion is at least 30 percent;
   (3) at least 90 weight percent of the palladium is located on the alumina at a depth less than 100 microns from the surface of the alumina; and
   (4) the crystalline phase of the alumina is alpha, theta, delta or a mixture thereof.

6. Process according to claim 5 for the preparation of dimethyl 1,4-cyclohexanedicarboxylate wherein a solution of dimethyl 1,4-benzenedicarboxylate in dimethyl 1,4-cyclohexanedicarboxylate is contacted with hydrogen.

7. Process according to claim 5 for the preparation of dimethyl 1,3-cyclohexanedicarboxylate wherein a solution of dimethyl 1,3-benzenedicarboxylate in dimethyl 1,3-cyclohexanedicarboxylate is contacted with hydrogen.

8. Process according to claim 5 for the preparation of dimethyl 1,2-cyclohexanedicarboxylate wherein a solution of dimethyl 1,2-benzenedicarboxylate in dimethyl 1,2-cyclohexanedicarboxylate is contacted with hydrogen.

* * * * *